(12) United States Patent
Zhou et al.

(10) Patent No.: US 7,780,987 B2
(45) Date of Patent: Aug. 24, 2010

(54) CONTROLLED RELEASE DOSAGE FORMS

(75) Inventors: Fang Zhou, Centreville, VA (US); Paul Maes, Potomac, MD (US)

(73) Assignee: Biovail Laboratories International SRL, St. Michael (BB)

( * ) Notice: Subject to any disclaimer, the term of this patent is extended or adjusted under 35 U.S.C. 154(b) by 761 days.

(21) Appl. No.: 10/370,109

(22) Filed: Feb. 21, 2003

(65) Prior Publication Data
US 2004/0037883 A1 Feb. 26, 2004

Related U.S. Application Data

(60) Provisional application No. 60/357,851, filed on Feb. 21, 2002.

(51) Int. Cl.
A61K 9/30 (2006.01)
A61K 9/28 (2006.01)
A61K 9/48 (2006.01)
A61K 9/32 (2006.01)

(52) U.S. Cl. .................. 424/475; 424/463; 424/474; 424/479; 424/480; 424/482

(58) Field of Classification Search .................. 424/451, 424/464
See application file for complete search history.

(56) References Cited

U.S. PATENT DOCUMENTS

| | | | |
|---|---|---|---|
| 3,097,144 A * | 7/1963 | Banker ........................ 424/482 |
| 4,800,087 A * | 1/1989 | Mehta ......................... 424/497 |
| 4,954,350 A * | 9/1990 | Jones et al. .................. 424/493 |
| 5,055,306 A * | 10/1991 | Barry et al. .................. 424/482 |
| 5,204,121 A | 4/1993 | Bucheler et al. |
| 5,288,505 A | 2/1994 | Deboeck et al. |
| 5,292,522 A * | 3/1994 | Petereit et al. ............... 424/490 |
| 5,458,888 A | 10/1995 | Chen |
| 5,478,573 A * | 12/1995 | Eichel et al. ................. 424/480 |
| 5,552,152 A | 9/1996 | Shen |
| 5,639,476 A * | 6/1997 | Oshlack et al. .............. 424/468 |
| 5,672,359 A * | 9/1997 | Digenis et al. ............... 424/463 |
| 5,733,575 A * | 3/1998 | Mehra et al. ................. 424/480 |
| 5,788,987 A | 8/1998 | Busetti et al. |
| 5,871,776 A | 2/1999 | Mehta |
| 5,891,474 A | 4/1999 | Busetti et al. |
| 6,022,554 A * | 2/2000 | Lee et al. ..................... 424/423 |
| 6,056,977 A * | 5/2000 | Bhagwat et al. ............. 424/488 |
| 6,143,326 A | 11/2000 | Möckel et al. |
| 6,156,342 A | 12/2000 | Sriwongjanya et al. |
| 6,183,779 B1 * | 2/2001 | Ouali et al. .................. 424/472 |
| 6,254,887 B1 | 7/2001 | Miller et al. |
| 6,303,146 B1 * | 10/2001 | Bonhomme et al. ......... 424/465 |
| 6,419,956 B1 | 7/2002 | Sue et al. |
| 6,451,350 B1 * | 9/2002 | Bartholomaeus et al. .... 424/490 |
| 6,569,457 B2 | 5/2003 | Ullah et al. |
| 6,576,260 B2 * | 6/2003 | Bartholomaeus et al. .... 424/469 |
| 6,620,439 B1 * | 9/2003 | Mehta ......................... 424/497 |
| 6,645,527 B2 * | 11/2003 | Oshlack et al. .............. 424/468 |
| 6,676,966 B1 | 1/2004 | Odidi et al. |
| 6,749,867 B2 | 6/2004 | Robinson et al. |
| 6,827,947 B2 | 12/2004 | Lofroth et al. |
| 6,866,866 B1 | 3/2005 | Chen et al. |
| 6,902,746 B2 | 6/2005 | Lee et al. |
| 6,994,873 B2 | 2/2006 | Valducci et al. |
| 2001/0046504 A1 | 11/2001 | Engel et al. |
| 2002/0051818 A1 | 5/2002 | Ullah et al. |
| 2003/0086971 A1 | 5/2003 | Kou |
| 2003/0099700 A1 | 5/2003 | Faham et al. |
| 2003/0104049 A1 | 6/2003 | Sherman |
| 2003/0104062 A1 | 6/2003 | Berner et al. |
| 2003/0118647 A1 | 6/2003 | Seth |
| 2003/0143270 A1 * | 7/2003 | Deboeck et al. ............. 424/468 |
| 2003/0157166 A1 | 8/2003 | Chen et al. |
| 2003/0211154 A1 | 11/2003 | Mukherji et al. |
| 2004/0005358 A1 | 1/2004 | Slugg et al. |
| 2004/0022755 A1 | 2/2004 | Kamath |
| 2004/0037883 A1 | 2/2004 | Zhou et al. |
| 2004/0058001 A1 | 3/2004 | Holzer et al. |
| 2004/0096499 A1 | 5/2004 | Vaya et al. |
| 2004/0096501 A1 | 5/2004 | Vaya et al. |
| 2004/0096502 A1 | 5/2004 | Platteeuw |
| 2004/0126428 A1 | 7/2004 | Hughes et al. |
| 2004/0161461 A1 | 8/2004 | Seth et al. |
| 2004/0185097 A1 | 9/2004 | Kannan et al. |
| 2004/0241236 A1 | 12/2004 | Li et al. |
| 2005/0019408 A1 | 1/2005 | Thumbeck et al. |
| 2005/0025829 A1 | 2/2005 | Kim |
| 2005/0042290 A1 | 2/2005 | Kerc et al. |
| 2005/0048118 A1 | 3/2005 | Cucala Escoi et al. |
| 2005/0084531 A1 | 4/2005 | Desai et al. |
| 2005/0123596 A1 | 6/2005 | Kohane et al. |
| 2005/0136109 A1 | 6/2005 | Rowley et al. |
| 2005/0136111 A1 | 6/2005 | Glinecke et al. |
| 2005/0238719 A1 | 10/2005 | Buzsaky |
| 2005/0271778 A1 | 12/2005 | Petereit et al. |

FOREIGN PATENT DOCUMENTS

| | | |
|---|---|---|
| EP | 0 386 440 | 9/1990 |
| EP | 1 112 738 | 7/2001 |
| EP | 1123700 A1 * | 8/2001 |
| JP | 01319417 A * | 12/1989 |
| WO | WO98/27967 | 7/1998 |
| WO | WO0056266 | 9/2000 |
| WO | WO 01/49270 | 12/2001 |

* cited by examiner

*Primary Examiner*—S. Tran
(74) *Attorney, Agent, or Firm*—Oblon, Spivak, McClelland, Maier & Neustadt, L.L.P.

(57) ABSTRACT

The invention provides stable controlled release monolithic coating compositions for use in coating pharmaceutical oral dosage forms comprising a polyglycol having a melting point greater than 55° C. and an aqueous dispersion of a neutral ester copolymer lacking functional groups.

6 Claims, No Drawings

CONTROLLED RELEASE DOSAGE FORMS

RELATED APPLICATIONS

This application claims priority from U.S. provisional patent application No. 60/357,851 filed Feb. 21, 2002.

FIELD OF THE INVENTION

This invention relates to a novel monolithic film coating for obtaining controlled release of drugs from oral dosage forms.

BACKGROUND

The manner in which chemicals or drugs are administered has gained increasing attention in the past two decades. Normally, a chemical is administered in a high dose at a given time only to have to repeat that dose several hours or days later. This is not economical and sometimes results in damaging side effects. As a consequence, increasing attention has been focused on methods of giving drugs continually for prolonged time periods and in a controlled fashion. Controlled or sustained release dosage forms provide a therapeutic dose of the drug soon after administration, and then gradually release the drug over an extended period of time. The primary method of accomplishing this controlled release has been through incorporating the drugs within polymers or to surround or encapsulate a core comprising the drug with a polymer coat. Depending on the type and amount of drug, as well as the type and amount of polymer and other pharmaceutically acceptable excipients the desired controlled release profile can be obtained.

The majority of polymers used to develop coatings for controlled release dosage forms are hydrophobic and can be applied either dry, from a solution, or suspension. As most of these polymers are poorly soluble in water, they are usually applied by dissolving the polymer in an organic solvent and then sprayed onto the drug core and evaporating off the solvent. The use of organic solvents, however, is considered problematic for several reasons. The most obvious reason relates to the safety hazards associated with the use of organic solvents. Organic solvents in general are highly flammable and carcinogenic. Further, organic solvents are expensive and the storage, disposal and use of organic solvents raise environmental concerns. Accordingly, it would be desirable to prepare aqueous suspensions or solutions of controlled release coatings comprising hydrophobic polymers suitable for coating a wide variety of drug cores.

Eudragit® NE30D, which contains 30% solids, is one of the first aqueous polymeric dispersions used for coating pharmaceutical dosage forms. Eudragit® NE30D has many advantages over other polymers for use as a film former for obtaining a controlled release drug profile and is thus ideally suited for controlled or sustained release drug formulations. The polymer forms a soft, flexible film at room temperature without any plasticizer. Also, no reactions or absorptive effects are observed when the polymer comes in direct contact with a therapeutically active agent. It is prepared by emulsion polymerization and consists of neutral copolymers of ethyl acrylate-methyl methacylate esters that are insoluble over the entire physiological pH range but will still swell in water and give permeable membranes. The permeability is independent of pH and is thus suitable for the development of pH-independent modified-release oral dosage forms, provided that the solubility of the drug is also pH-independent.

One of the most significant differences between aqueous polymeric solutions and dispersions is the role water plays during film formation. In solutions, water is a solvent and drying is accompanied by an excessive increase in viscosity, which in turn suppresses the rate of evaporation. Excess energy is therefore required to drive off the water. In contrast, in polymeric dispersions such as Eudragit® NE30D, water is only a dispersion medium and does not solvate the polymers. Consequently, less heat is needed to evaporate the water. Fast water evaporation coupled with the high solids content of the dispersion significantly reduces processing time. These properties are especially critical when dealing with highly water-soluble or moisture sensitive therapeutically active agents.

The pigment binding capacity of Eudragit® NE30D is very high, so that up to ~2-3 parts by weight of additives can be incorporated into 1 part by weight of dry polymer without affecting the film properties. The polymer is also compatible with a wide variety of pharmaceutical excipients.

Plasticizers are generally added to coating formulations to modify the physical properties i.e., the glass transition temperature (Tg) of the polymer to make it more usable. The Tg is the temperature at which an amorphous polymer (or the amorphous regions in a partially crystalline polymer) changes from a hard and relatively brittle condition to a viscous or rubbery condition. Plasticizers function by decreasing the Tg of the polymer so that under ambient conditions the films are softer, more pliable and often stronger, and thus better able to resist mechanical stress. Eudragit® NE30D, however, has a low Tg and accordingly does not require the use of plasticizers. In fact, addition of plasticizers can be detrimental as it can increase the viscosity of the Eudragit® NE30D formulation and negate one of the distinct advantages of the dispersion over the polymeric solution. Incorporation of plasticizers into Eudragit® NE30D formulations can also increase the tackiness of the coat and complicate the coating process (Ghebre-Sellassie and Nesbit. *Application of Eudragit E30D in Controlled-Release Coatings* in Aqueous Polymeric Coatings for Pharmaceutical Forms, J. McGinity Ed., 1989, Marcel Dekker, Inc., pp 247-266).

Due to its low Tg, Eudragit® NE30D is sensitive to excessive drying conditions or exposure to high temperatures. Ghebre-Sellassie and Nesbit (*Application of Eudragit E30D in Controlled-Release Coatings* in Aqueous Polymeric Coatings for Pharmaceutical Forms, J. McGinity Ed., 1989, Marcel Dekker, Inc., pp 247-266) state that excessive drying of Eudragit® NE30D coats can be detrimental as such conditions do not allow the coating formulation to spread out evenly and promote particle deformation and coalescence. Also, during the coating process, the product temperature should be kept at around 26° C. If the product temperature is very high, the coating material becomes tacky owing to the low Tg of Eudragit® NE30D, which leads to agglomeration of the coated product. Ghebre-Sellassie and Nesbit also emphasize that Eudragit® NE30D coated products should not be stored at temperatures above 40° C., as stability tests conducted at elevated temperatures may not correlate with the long-term behavior of Eudragit® NE30D coated products at room temperature.

Attempts have been made in the prior art to design microporous aqueous polymer coatings suitable for use on drug cores to obtain controlled or sustained release profiles using the Eudragits, and in particular Eudragit® NE30D. U.S. Pat. No. 5,529,791 for example, teaches controlled release dosage forms of Diltiazem in which the Diltiazem drug core is surrounded by a water-soluble and/or dispersible film forming polymer or copolymer constituting the microporous membrane. The polymers or copolymers taught include the polyacrylates and polymethacrylates of the Eudragit type, such as Eudragit NE30D, L30D, and RS30 D, ethylcelluloses, hydroxypropyl cellulose and hydroxypropylmethylcellulose and their derivatives. In addition to the polymer or copolymer, the microporous membrane contains, preferably, talc and/or magnesium stearate as a lubricant, polyvinylpyrrolidone as a plasticizer, titanium dioxide as a pigment, Tween 80 as an emulsifier, and silicone oil as an antifoaming agent. Other plasticizers taught include triacetin, dibutylpthalate, dibutylsebacate, citric acid esters, polyethyleneglycols, and polypropyleneglycols. The Eudragit® NE30D coated beads were cured for 16 hours at 50° C. (Example 3) or for 15 hours at 45° C., 5-10° C. beyond the recommended temperature for Eudragit® NE30D. Further, long-term stabilization data was not presented for the coated products, and accordingly, it is not known what effect the elevated temperature had, if any, on the stability of the controlled release dosage form of Diltiazem.

U.S. Pat. No. 5,286,493 is directed to stabilized controlled release formulations having an aqueous acrylic polymer coating. The '493 patent also teaches the use of controlled release coatings covering a solid dosage form. The coating is derived from aqueous dispersions of an acrylic resin, which provides a substantially stable release pattern of a drug from the dosage form. The acrylic resins taught are the ammonio methacrylate co-polymers as for example Eudragit® RL30D, RS30D and combinations thereof. The acrylic coatings include an effective amount of a suitable plasticizing agent. The stable Eudragit® RL30D and/or RS30D coated products are cured at temperatures above the Tg of the acrylic polymers. The '493 patent does not teach the use of Eudragit® NE30D.

U.S. Pat. No. 5,478,573 teaches delayed, sustained-release propranolol pharmaceutical preparations purportedly achieved by surrounding a water-soluble drug core with a hydratable diffusion barrier which delays drug release by for about 2-10 hours. The hydratable diffusion barrier is said to comprise a film-forming polymer such as acrylic resin or ethyl cellulose or mixtures thereof and an additive which controls the rate of hydration and permeability of the diffusion barrier. The preferred insoluble film-forming polymers are aqueous dispersions of fully esterified acrylic resins such as Eudragit® NE30D. The additives controlling the rate of hydration and permeability of the diffusion barrier are preferably selected from the group consisting of fully esterified acryclic resins containing quaternary amine side chains, anionic surfactants, lubricants, plasticizers, inert water soluble materials and mixtures thereof. The '573 patent teaches that the drug beads coated with the aqueous polymeric dispersion are dried at 35° C. to 60° C. for 8 hours to 5 days. No data is presented on the long-term stability of the products.

Another controlled release pharmaceutical dosage form using an aqueous acrylic polymer dispersion is taught in U.S. Pat. No. 5,871,776. The controlled release profile is obtained, however, using multiple layers of films. The outermost layer is comprised of the aqueous acrylic polymer dispersion. The preferred acrylic polymer is Eudragit® NE30D. The coatings may also contain other pharmaceutically acceptable excipients such as fillers, anti-adherents, pharmaceutically acceptable pigments and lubricants/glidants. The coated drug pellets are cured at a temperature in the range of from about 30° C. to about 50° C., preferably from about 35° C. to about 45° C. and most preferably about 40° C. for a period of about 5 to about 10 days, an preferably about 7 days. The inventors surprisingly found that in contrast to the preferred short curing times taught in the prior art, long curing times help stabilize the release of the drug from the coated pellets after long storage periods.

International Patent Publication No. WO 02/058677 describes a film coating composition comprising an aqueous acrylic polymer dispersion, a surfactant, and sodium stearyl fumarate. The acrylic polymer dispersion is preferably Eudragit® NE30D. There does not appear to be any teaching as to the curing temperature and furthermore no data is presented with regard to long-term stability of the coated product.

In summary, it would seem that although the prior art teaches the use of aqueous acrylic dispersion coatings of Eudragit® NE30D, in most part, the prior art does not seem to have overcome long term stability problems of products coated with aqueous Eudragit® NE30D dispersions. Where the products have been found to be stable, the length of curing is very long and this is inefficient to the manufacturing process and also raises problems with storage of scale-up product. Accordingly, and given the advantages and versatility of Eudragit® NE30D, it would desirable that a stable controlled or sustained release coat be developed with short curing times to enhance process times. It is therefore an object of this invention to develop such a product.

SUMMARY OF THE INVENTION

This invention is related to a novel monolithic stable controlled release coating for use in coating oral pharmaceutical dosage forms.

In one aspect, the coating comprises an aqueous dispersion of a neutral ester copolymer without any functional groups; a poly glycol having a melting point greater than 55° C., and one or more pharmaceutically acceptable excipients; wherein said coating composition is coated onto said oral pharmaceutical dosage forms and cured at a temperature at least equal to or greater than the melting point of the poly glycol.

In another aspect, the invention provides a controlled release dosage form comprising a core, wherein the core comprises an effective amount of at least one therapeutically active agent, and one or more first pharmaceutically acceptable excipients, and a stable controlled release monolithic coating composition for coating said core, said coating comprising an aqueous dispersion of a neutral ester copolymer without any functional groups; a poly glycol having a melting point greater than 55° C., and one or more pharmaceutically acceptable excipients; wherein said coating composition is coated onto said oral pharmaceutical dosage forms and cured at a temperature at least equal to or greater than the melting point of the poly glycol.

In one embodiment, the neutral ester copolymer without any functional groups is selected from the group consisting of Eudragit® NE30D and Eudragit® NE40D. Preferably, the neutral ester copolymer without any functional groups is Eudragit® NE30D. The neutral ester copolymer without any functional groups is present in an amount from about 1% to about 35% by weight of the coating composition.

In one embodiment, the poly glycol is selected from the group consisting of polyethylene glycol 6000, polyethylene glycol 8000, polyethylene glycol 10000 and polyethylene glycol 20000. The poly glycol is present in an amount of from about 0.01% to about 10% by weight of the coat composition, or from about 0.01% to about 3% by weight of the coat composition, or from about 0.01% to about 0.5% by weight of the coat composition. Preferably, the poly glycol is polyethylene glycol.

The addition of pharmaceutically acceptable excipients to the coating composition is contemplated and can include anti-tacking agents, emulsifying agents, hydrophilic agents, anti-foaming agents, flavourants, colorants, sweeteners and any combination thereof. The preferred anti-tacking agent is talc, the preferred hydrophilic agent is hydroxypropyl methycellulose, the preferred anti-foaming agent is simethicone, the preferred emulsifying agent is polyoxyethylene sorbitan mono-oleate, and the preferred colorant is titanium dioxide. In another embodiment the amount of neutral ester copolymer may range from about 1% to about 25% by weight of the coating compositions or about 1% to about 7% by weight of the coating composition. In another embodiment the amount of polyethylene glycol may range from about 0.1% to 10%, or about 0.1% to 5% or about 0.1 to 3% or about 0.1 to 0.5% by weight of the coating composition. In another embodiment the amount of hydrophilic agent in the coating may range from about 0.1 to 6% or about 0.1% to 3% by weight of the coating composition. In another embodiment the invention is directed to a pharmaceutical dosage form comprising a stable controlled release monolithic coating, said coating comprising an aqueous dispersion of Eudragit® NE30D, polyethylene glycol 8000, hydroxypropyl methylcellulose, talc, simethicone, titanium dioxide, and polyoxyethylene sorbitan mono-oleate, said Eudragit® NE30D is present in an amount of from about 1% to about 35% by weight of the coat composition, said polyethylene glycol is present in an amount of from about 0.1% to about 3% by weight of the coat composition, said hydroxypropyl methylcellulose is present in an amount of from about 0.1% to about 6% by weight of the coat composition, said talc is present in an amount of from about 0.1% to about 7% by weight of the coat composition, said simethicone is present in an amount up to about 0.5% by weight of the coat composition, said polyoxyethylene sorbitan mono-oleate is present in an amount of up to about 0.5% by weight of the coat composition, said titanium dioxide is present in an amount of from about 0.% to about 2% by weight of the coat composition; and composition is coated onto said pharmaceutical oral dosage form and cured at a temperature at least equal to or greater than the melting point of said polyglycol wherein said dosage form may be a tablet or a capsule.

DETAILED DESCRIPTION OF THE INVENTION

The present invention is directed to novel aqueous dispersions of neutral ester copolymers without any functional groups suitable for use as coatings for controlled or sustained release drug dosage forms. The coating formulation is quite versatile in that it can be used to coat a variety of drug cores and can be easily manipulated to obtain the desired drug release profile. In another embodiment, the invention consists of a controlled release pharmaceutical composition, in one embodiment, a tablet, comprising at least one form of a therapeutically active agent, wherein the pharmaceutical composition comprises a core and a stable controlled release coating of the invention.

I. Cores

The core comprises an effective amount of a therapeutically active agent and at least one pharmaceutically acceptable excipient, in one embodiment a lubricant, a binder and/or filler, and optionally a glidants as well as other pharmaceutically acceptable excipients.

A wide variety of therapeutically active agents is contemplated. These include but are not limited to anti-tussives, anti-histamines, decongestants, alkaloids, mineral supplements, vitamins, antacids, ion exchange resins, anti-cholesterolemics, anti-lipid agents, anti-arrhythmics, anti-pyretics, analgesics, appetite suppressants, anti-depressants, expectorants, anti-anxiety agents, anti-ulcer agents, anti-inflammatory substances, coronary dilators, opioid agonists, cerebral dilators, peripheral vasodilators, antibiotics, anti-virals, psycho-tropics, anti-manics, stimulants, gastrointestinal agents, sedatives, anti-diarrheal agents, anti-anginal drugs, vasodilators, anti-hypertensive drugs, vasoconstrictors, migraine treatments, anti-infectives, tranquilizers, anti-psychotics, anti-tumor drugs, anticoagulants, antithrombic drugs, hypnotics, anti-emetics, anti-nauseants, anti-convulsants, neuromuscular drugs, hyper- and hypoglycemic agents, thyroid and anti-thyroid agents, diuretics, anti-spasmodics, uterine relaxants, mineral and nutritionaql additives, anti-obesity drugs, anabolic drugs, erythropoietic drugs, anti-asthmatics, cough suppressants, mucolytics, $H_2$-antagonists, anti-uricemic drugs. Mixtures are operable depending on the type of drugs. The skilled artisan will know, based on his technical knowledge, which drug combinations are acceptable. The therapeutically active agent(s) are present in an amount from about 5% to about 99% by weight of the cores. The amount present is highly dependent on the agent(s), the desired controlled release profile, and the strength of the desired dosage form. Different forms of the therapeutically active agent are also contemplated. One form of the therapeutically active agent may be the individually optically active enantiomers of the therapeutically active agent. Pharmaceutically acceptable salts, as for example pharmaceutically acceptable addition salts, of the therapeutically active agent(s) are also suitable. Suitable pharmaceutically acceptable addition salts may be the hydrochloride salt, the hydrobromide salt, the hydroiodide salt, the saccharinate salt etc.

Glidants improve the flowabilitye of the excipient powder by reducing intraparticulate friction. This is especially important during tablet production at high production speeds and during direct compaction. Examples of glidants include but are not limited to starch, talc, lactose, stearates (such as for example magnesium stearate), dibasic calcium phosphate, magnesium carbonate, magnesium oxide, calcium silicate, Cabosil™, colloidal silica (Syloid™) and silicon dioxide aerogels. Glidants, if present, range in amounts from greater than about 0% to about 20%, with amounts of about 0.1% to about 5% being typical.

Lubricants ensure that tablet formation and ejection can occur with low friction between the solid and the die wall. High friction during tabletting can cause a series of problems, including inadequate tablet quality (capping or even fragmentation of tablets during ejection, and vertical scratches on tablet edges) and may even stop production. Lubricants are thus included in almost all tablet formulations. Such lubricants include but are not limited to adipic acid, magnesium stearate, calcium stearate, zinc stearate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil and the like may be employed, with sodium stearyl fumarate being preferred. Waxy fatty acid esters, such as glyceryl behenate, sold as "Compritol™" products, can be used. Other useful commercial lubricants include "Stear-O-Wet™" and "Myvatex™ TL". Mixtures are operable. Lubricants are used in amounts typically ranging from greater than about 0% to about 10%, with about 0.01% to about 5.0% by weight of the tablet preferred.

It is well known in the art that besides reducing friction, lubricants may cause undesirable changes in the properties of a tablet. The presence of a lubricant in the excipient powder is thought to interfere in a deleterious way with the bonding between the particles during compaction and thus reduce tablet strength. Because many lubricants are hydrophobic, tablet disintegration and dissolution are often retarded by the addition of a lubricant. Such negative effects are strongly related to the amount of lubricant present. Other considerations known in the art include the manner in which a lubricant is mixed, the total mixing time and the mixing intensity. In order to avoid these negative effects, hydrophilic substances may be substituted for the hydrophobic lubricants. Examples include, but are not limited to, surface-active agents and polyethylene glycol. A combination of hydrophilic and hydrophobic substances can also be used.

Anti-adherents reduce adhesion between the excipient powder mixture and the punch faces and thus prevent particles sticking to the punches, a phenomenon know in the art as "sticking" or "picking", and is affected by the moisture content of the powder. One example of antiadherent is microcrystalline cellulose. Many lubricants such as magnesium stearate have also antiadherent properties. However, other substances with limited ability to reduce friction can also act as antiadherents. Such substances include for example talc and starch. Mixtures are operable. Antiadherents, if present, range from about 0% to about 20% by weight of the tablet depending on the antiadherent being used.

Sorbents are substances that are capable of sorbing some quantities of fluids in an apparently dry state. Thus, oils or oil-drug solutions can be incorporated into a powder mixture, which is granulated and compacted into tablets. Other examples of sorbing substances include microcrystalline cellulose and silica.

Diluents or fillers are added to increase the bulk weight of the blend resulting in a practical size for compression. The ideal diluent or filler should fulfill a series of requirements, such as: be chemically inert, be non-hygroscopic, be biocompatible, possess good biopharmaceutical properties (e.g. water soluble or hydrophilic), good technical properties (such as compactibility and dilution capacity), have an acceptable taste and be cheap. As a single substance cannot fulfill all these requirements, different substances have gained use as diluents or fillers in tablets.

Lactose is a common filler in tablets. It possesses a series of good filler properties, e.g. dissolves readily in water, has a pleasant taste, is non-hygroscopic and fairly non-reactive and shows good compactibility. Other sugars or sugar alcohols, such as glucose, sucrose, sorbitol and mannitol, have been used as alternative fillers to lactose, primarily in lozenges or chewable tablets because of their pleasant taste. Mannitol has a negative heat of solution and imparts a cooling sensation when sucked or chewed.

Apart from sugars, perhaps the most widely used fillers are celluloses in powder forms of different types. Celluloses are biocompatible, chemically inert, and have good tablet forming and disintegrating properties. They are therefore used also as dry binders and disintegrants in tablets. They are compatible with many drugs but, owing to their hygroscopicity, may be incompatible with drugs prone to hydrolyse in the solid state. The most common type of cellulose powder used in tablet formulation is microcrystalline cellulose.

Another important example of a diluent or filler is dibasic and tribasic calcium phosphate, which is insoluble in water and non-hygroscopic but is hydrophilic, i.e. easily wetted by water. Other examples of diluents include but are not limited to di- and tri-basic starch, calcium carbonate, calcium sulfate, and modified starches. Many diluents are marketed in "direct compression" form, which adds other desirable properties, such as flow and binding. There are no typical ranges used for the diluents, as targeted dose and size of a tablet are variables that influence the amount of diluent that should be used.

Binders (also sometimes called adhesives) are added to ensure that tablets can be formed with the required mechanical strength. Binders can be added in different ways: (1) As a dry powder, which is mixed with other ingredients before wet agglomeration; (2) As a solution, which is used as agglomeration liquid during wet agglomeration. Such binders are often referred to as "solution binders", and (3) As a dry powder, which is mixed with the other ingredients before compaction (slugging or tabletting). Such binders are often referred to as "dry binders". Common traditional solution binders are starch, sucrose, and gelatin. More commonly used binders with improved adhesive properties, are polymers such as polyvinylpyrrolidone and cellulose derivates such as for example hydropropyl methylcellulose. Examples of dry binders include microcrystalline cellulose and crosslinked polyvinylpyrrolidone. Other examples of binders include but are not limited to pregelatinized starches, methylcellulose, sodium carboxymethylcellulose, ethylcellulose, polyacrylamides, polyvinyloxoazolidone and polyvinylalcohols. Binders, if present, range in amounts from about greater than about 0% to about 25% depending on the binder used.

The manufacturing process of the core can be as follows. The at least one therapeutically active agent is first granulated with the at least one binder, in one embodiment a granulator, but not necessarily a fluidized bed granulator. The at least one binder is first dissolved or dispersed in a suitable solvent, in one embodiment water. The solution or suspension of the at least one binder is then sprayed onto the at least one therapeutically active agent in a granulator, in one embodiment a fluidized bed granulator. For example, fluidized bed granulators manufactured by Glatt (Germany) or Aeromatic (Switzerland) can be used for this operation. An alternative process can be to use a conventional or high shear mixer for granulation. If necessary, the at least one therapeutically active agent can be mixed with a filler, prior to the granulation step. Granules once dried can be mixed with the other pharmaceutically acceptable excipients, especially with the at least one lubricant, but also with at least one glidant and any other pharmaceutically acceptable excipient suitable to improve processing. The mixture of granules (in one embodiment with the at least one lubricant), and optionally at least one glidant is pressed into tablets. Alternatively, the at least one therapeutically active agent and the at least one lubricant can be mixed in a granulator, in one embodiment a fluidized bed granulator, and heated to the melting point of the at least one lubricant to form granules. This mixture can then be mixed with at least one suitable filler and compressed into tablets. Also, it is possible to mix the at least one therapeutically active agent and the at least one lubricant (in one embodiment polyvinyl alcohol) in a granulator, in one embodiment a fluidized bed granulator, and then to press the resulting granules into tablets. Tablets can be obtained by standard techniques, in one embodiment on a (rotary) press (for example Manesty Betapress®) fitted with suitable punches. The resulting tablets are hereinafter referred as tablet cores.

The tablet cores are then coated with the semi-permeable coating designed to achieve a controlled release of the at least one therapeutically active agent.

II. Coating Formulation

Particularly useful neutral ester copolymers without any functional groups constituting the coat of the invention described herein are Eudragit® NE30D, Eudragit® NE40D (Rohm America LLC). The preferred polymer is Eudragit NE30D and is present in an amount of from about 1% to about 35% by weight of the coat depending on the therapeutically active agent used and the controlled release profile desired. Hydrophilic agents may also be included in the coat to promote wetting of the coat when in contact with gastrointestinal fluids. Such hydrophilic agents include hydrophilic water soluble polymers such as hydroxypropyl methylcellulose (HPMC), hydroxypropyl cellulose (HPC) and combinations thereof. HPMC is the preferred hydrophilic water soluble polymer. If hydrophilic agents are to be included in the coat composition the agents should be present in an amount from about 0.1% to about 10% by weight of the coating composition, preferably from about 0.1% to about 5% by weight of the coating composition and most preferably from about 0.1% to about 3% by weight of the coating composition.

The coat formulation also comprises a poly gycol with a melting point of greater than 55° C. The poly glycol is selected from the group consisting of polyethylene glycol 6000, polyethylene glycol 8000, polyethylene glycol 10000, and polyethylene glycol 20000. The preferred poly glycol is polyethylene glycol 8000. The poly glycol is present in an amount of from about 0.1% to about 5% by weight of the coat. Other suitable polyglycol derivatives having a melting point at least of 55 deg C. can be, but are not limited to, Poloxamer 188, Poloxamer 338, Poloxamer 407, Polyethylene Oxides, Polyoxyethylene Alkyl Ethers, and Polyoxyethylene Stearates.

In addition to the copolymers and the poly glycol, the coating formulation comprises other pharmaceutically acceptable excipients. The excipients can include but are not limited to anti-tacking agents, emulsifying agents, antifoaming agents, flavourants, colourants, etc. It is known in the art that depending on the intended main function, excipients can affect the properties of the coat in a series of ways, and many substances used in coat formulations can thus be described as multifunctional. A skilled worker will know, based on his technical knowledge, which pharmaceutically acceptable excipients are suitable for the desired controlled release coating composition.

The tackiness of polymeric films is important for the coating of solid dosage forms and for the subsequent curing step (post coating thermal treatment). During coating with either cellulosic or acrylic polymers, an unwanted, and sometimes irreversible agglomeration of several granules or beads or, in the worst case, of the complete batch, can occur, especially at higher product processing temperatures. Accordingly, the addition of anti-tacking agents to coating formulations is desirable. The anti-tacking agents which can be used include but are not limited to adipic acid, magnesium stearate, calcium stearate, zinc stearate, hydrogenated vegetable oils, sterotex, glyceryl monostearate, talc, sodium benzoate, sodium lauryl sulfate, magnesium lauryl sulfate, and the like may be employed. Talc is the preferred anti-tacking agent. Talc may also function as a wetting agent. Mixtures of the anti-tacking agents are operable. The amount of anti-tacking agent in the coating composition is preferably in the range from about 1% to about 15% by weight of the coating dispersion and more preferably from about 1% to about 7% by weight of the coating dispersion.

The anti-foaming agents, which may be included in the coating composition of the invention include silicon oil or simethicone, with simethicone being the preferred anti-foaming agent. The anti-foaming agent, if present, is present in an amount up to about 0.5% by weight of the coat composition and preferably from about 0.1% to about 0.4% by weight of the coating composition.

The inclusion of an emulsifying agent or agents (also called emulsifiers or emulgents) is necessary to facilitate actual emulsification during manufacture of the coat, and also to ensure emulsion stability during the shelf-life of the product. Emulsifying agents useful for the coat composition of the invention include, but are not limited to naturally occurring materials and their semi synthetic derivatives, such as the polysaccharides, as well as glycerol esters, cellulose ethers, sorbitan esters and polysorbates. Mixtures are operable. The preferred emulsifying agent is Polysorbate 80 (polyoxyethylene sorbitan mono-oleate)(Tween 80). The emulsifying agent or agents are present in an amount up to about 0.5% by weight of the coat composition and preferably from about 0.1% to about 0.3% by weight of the coat composition.

Any permitted colourants in a film coat formula are invariably water-insoluble colors (pigments). Pigments have certain advantages over water-soluble colors in that they tend to be more chemically stable towards light, provide better opacity and covering power, and optimize the impermeability of a given film to water vapor. Examples of suitable colorants include, but are not limited to iron oxide pigments, titanium dioxide, and aluminum Lakes. Mixtures are operable. The preferred pigment is titanium dioxide. The pigment or colorant is present in an amount of from about 0.1% to about 10% by weight of the coat composition, preferably from about 0.1% to about 5% by weight of the coat composition and most preferably from about 0.1% to about 2% by weight of the coat composition.

The coating may be applied onto a core comprising an effective amount of the therapeutically active agent by a process, which involves the atomization (spraying) of the coating solution or suspension onto a bed of the tablet cores. Some examples of equipment suitable for film coating include: Accela Cota (Manesty Machines, Liverpool, UK), Hi-Coater (Freund Company, Japan), Driacoater (Driam Metallprodukt GmbH, Germany), HTF/150 (GS, Italy), and IDA (Dumoulin, France). Examples of units that function on a fluidized-bed principle include: Aeromatic (Fielder, Switzerland and UK) and Glatt AG (Switzerland). The preferred and most widely used apparatus is the Accela Cota.

The coating fluid is delivered to the coating apparatus from a peristaltic pump at the desired rate and sprayed onto the rotating or fluidizing tablet cores. The tablet cores are pre-warmed to about 30° C. During the coating process, the product temperature range is maintained between about 25° C. and 35° C. by adjusting the flow rate of the inlet and outlet air, temperature of the inlet air and spray rate. A single layer of coat is applied and once spraying is complete, the coated tablet cores are dried between about 30° C. to about 40° C. for about 3-5 minutes at a low pan speed and low air flow. The pan was readjusted to jog speed, and drying continued for 12-15 minutes.

The coated tablet cores are placed onto a tray and cured (post coating thermal treatment) in an electrical or steam oven at a temperature above the temperature of the melting point of the polyethylene glycol or derivative thereof. The curing temperature is preferably greater than the melting point of the polyethylene glycol or derivative thereof. The curing time is preferably about 2 to about 7 hours. The cured coated tablets are subsequently cooled to room temperature.

The findings disclosed herein are particularly surprising in light of the prior art teachings with regard to Eudragit® NE30D. As mentioned above, Eudragit® NE30D has a low Tg and the use of plasticizers, such as polyethylene glycol or its derivatives, is not recommended. In fact, as mentioned above, the prior art teaches that the addition of plasticizers can be detrimental to Eudragit® NE30D. Surprisingly, however, applicants have found that addition of polyethylene glycol or its derivatives in the amounts described herein and curing the coated tablets at above the melting temperature of the polyethylene glycol provided for a controlled release of the therapeutically active agent. Moreover, the coated tablet cores were found to be stable over time. The desired dissolution profile obtained provides a controllable lag time such as in an S-shaped Weibull profile. This is a surprising result and is not taught in the prior art. The controlled lag time and the desired dissolution profile can be accomplished by a single coating.

As will be seen from the non-limiting examples described below, the coating of the invention is quite versatile. The length and time for the delay is controlled by rate of hydration and the thickness of the coat. The drug release rate subsequent to the delay is determined by the thickness and permeability of the hydrated coat. Thus, it is possible to regulate the rate of hydration and permeability of the coat so that the desired controlled-release drug profile can be achieved. There is no preferred coat thickness, as this will depend on the drug being used in the core and also the controlled release profile desired. Other parameters in combination with the thickness of the coat include varying the concentrations of some of the ingredients of the stable coat composition of the invention described and/or varying the curing temperature and length of curing the coated tablet cores. The skilled artisan will know which parameters or combination of parameters to change for a desired controlled release profile.

The following non-limiting examples illustrate the invention:

EXAMPLE 1

Metformin HCL Tablets 1.1 Tablet Core Preparation

The following formulation was prepared for Metformin HCl 500 mg strength tablets:

| Ingredients | % w/w |
|---|---|
| Metformin HCl | 95.70 |
| Silicon Dioxide* | 0.50 |
| Polyvinyl alcohol (PVA)** | 1.80 |
| Atomized Glyceryl Behenate*** | 2.00 |
| Total | 100.00 |

*Aerosil 200.
**The PVA is prepared as a 4% solution (w/w) in purified water. The purified water is not considered as part of the theoretical batch size since it is evaporated during drying of the core in the fluid bed granulator.
***Compritol 888 ATO All of the metformin and silicon dioxide was transferred to a V-blender and blended for about 10 min. The blended material was then discharged into a fluid bed granulator and granulation was carried out in the presence of the PVA solution under the following process parameters:

| | |
|---|---|
| Granulation Temperature (° C.) | 35-45 |
| Air Volume (m/s) | 0.5-3.0 |
| Atomization Air Pressure (Bar) | 0.5-2.0 |
| Fluid Spray Rate (g/min) | 3-11 |
| Drying Temperature (° C.) | 45-55 |

The LOD % of the granules after drying was NMT 3% as determined by moisture balance.

After drying, the granules were sized by passing the granules through a 0.71 mm screen. The screened granules were then transferred to a V-blender and blended with the remainder of the lactose and all of the atomized glyceryl behenate for about 10 min. Finally, the magnesium stearate was added and blending was carried out for about 5-10 more minutes.

The dissolution profile of the compressed tablet cores was determined under the following conditions:

Medium: 900 ml water

Method: USP Type II Apparatus, 50 rpm at 37° C.

The tablet cores are immediate release. The release of metformin HCl from the tablet cores was found to be about 100% in about 30 min.

1.2 Core Coating

The following three coating formulations were prepared:

| Ingredients | Coating MA (%) | Coating MB (%) | Coating MC (%) |
|---|---|---|---|
| Eudragit NE30D | 25.33 | 26.97 | 27.03 |
| Talc 400 | 6.84 | 5.30 | 5.32 |
| HPMC 606 | 5.98 | 2.47 | 2.25 |
| PEG 8000 | 2.14 | 2.25 | 2.25 |
| Titanium dioxide | 1.71 | 1.35 | 1.35 |
| Somethicone | 0.39 | 0.31 | 0.31 |
| Tween 80 | 0.34 | 0.23 | 0.23 |
| Purified Water | 57.27 | 61.12 | 61.26 |
| Total | 100.00 | 100.00 | 100.00 |

The metformin tablet cores were then coated with either one of the coating formulations. The coating process was carried out in a Glatt GPCG-1 apparatus equipped with a coating chamber without a Wuster column. The mesh size of the bottom screen was 200 μm and the size of the spray nozzle was 1 mm.

The coating formulation was prepared as follows:

| | Materials |
|---|---|
| Component A | Eudragit NE30D<br>Water |
| Component B | HPMC 606<br>Water |
| Component C | Simethicone<br>(DOW CORNING ®)<br>Water |
| Component D | Tween 80<br>Water |
| Component E | Component D + C |
| Component F | Talc<br>PEG 8000 (MT)<br>Titanium dioxide<br>Water |
| Final coating Dispersion G (A + B + C + D + E + F) | |

1.2.1 Preparation of Component A

Water is transferred to a stainless steel container of a Silverson high-shear mixer and the mixer turned on at continuous low speed to produce a sufficient mixer. All of the Eudragit NE 30D dispersion is added to the water and mixed for about 10 min using a Caframo Mixer.

1.2.2 Preparation of Component B

All of the Pharmacoat 606 is added to 65±5° C. water and mixed for about 5 min using a silverson high shear mixer at a low speed.

1.2.3 Preparation of Component C

All of the simethicone is placed in a 100 ml beaker to which 50 g of water is added and mixed to uniformity.

1.2.4 Preparation of Component D

All of the Tween 80 is transferred to a 100 ml beaker to which 50 g of water is added and mixed until all the Tween 80 is dissolved.

1.2.5 Preparation of Component E

Dispersion E is prepared by uniformly mixing component D and component C.

1.2.6 Preparation of Component F

Water is transferred to a stainless steel container of a Silverson high-shear mixer and the mixer turned on at continuous low speed to produce a sufficient vortex. The PEG is added gradually to the vortex and mixed until the all of the PEG is dissolved. Components B and E are next added and mixing is continued for 5 min. All of the talc and titanium dioxide is added and mixed for another 15 min.

1.2.7 Preparation Final Coating Dispersion G

Component F is slowly added component A while stirring.

The processing parameters for coating the tablet cores were as follows:

| Coating Temperature (° C.) | 30-32 |
| Air Volume (m/s) | 4.0-6.5 |
| Atomization Air Pressure (Bar) | 1.3-2.3 |
| Coating Fluid Spray Rate (g/min) | 3-6 |
| Drying Temperature (° C.)** | 30-35 |

**Coated tablets were dried for about 3 min.

After application of the coating the tablets were cured in an oven at 62±2° C. for about 2 hours. This temperature is above the melting temperature of the polyethylene glycol 8000.

The metformin tablet cores were next coated with either one of the coating formulations MA, MB, or MC to a weight gain of either 14% or 16% w/w by weight of the tablet core and cured in an oven at between about 60° C. to about 75° C. for between about 2 hours to about 15 hours.

Dissolution tests of the coated tablet cores was carried out under the following dissolution conditions:

Medium: 900 ml water.
Method: USP Type II Apparatus, 50 rpm at 37° C.

The results are presented in Table 1 as a % release into the medium of the total metformin HCl in the tablet:

TABLE 1

| Time (h) | Tablet cores coated with coating formulation MA to 16% weight gain | Tablet cores coated with coating formulation MB to 14% weight gain | Tablet cores coated with coating formulation MC to 14% weight gain |
| --- | --- | --- | --- |
| 0 | 0 | 0 | 0 |
| 1 | 21.15 | 11.26 | 7.04 |
| 2 | 50.35 | 24.4 | 16.59 |
| 3 | 73.8 | 38.12 | 26.69 |
| 4 | 89.73 | 52.75 | 38.02 |
| 5 | 98.65 | 66.73 | 50.56 |
| 6 | 102.24 | 79.25 | 63.31 |
| 7 | 103.55 | 88.78 | 74.98 |
| 8 | — | 95.41 | 84.71 |
| 9 | — | 99.42 | 91.92 |
| 10 | — | 101.76 | 96.47 |
| 11 | — | 103.05 | 99.45 |
| 12 | — | 103.86 | 101.21 |

A study was done to determine the effect of curing temperature and length of curing on drug dissolution. The curing temperature was set at 65° C. for 1, 2 and 5 hours. The effect on the dissolution of the drug at a curing temperature of 75° C. for about 2 hours was also determined. Dissolution tests of the coated tablets under the different curing temperatures and lengths of time were carried under the following dissolution conditions:

Medium: 900 ml water.
Method: USP Type II Apparatus, 50 rpm at 37° C.

The results are presented in Table 2 as a % release into the medium of the total metformin HCl in the tablet:

TABLE 2

| Time (h) | MB (65° C.-60 min) | MB (65° C.-120 min) | MB (65° C.-300 min) | MB (75° C.-120 min) |
| --- | --- | --- | --- | --- |
| 0 | 0 | 0 | 0 | 0 |
| 1 | 9.98 | 8.08 | 7 | 6.47 |
| 2 | 23.73 | 18.65 | 17.14 | 15.76 |
| 3 | 40.53 | 29.8 | 27.62 | 25.67 |
| 4 | 61.77 | 42.52 | 39.8 | 36.6 |
| 5 | 81.77 | 56.48 | 53.84 | 48.63 |
| 6 | 92.51 | 71.32 | 67.67 | 60.74 |
| 7 | — | 80.94 | 79.85 | 72.57 |
| 8 | — | 86.35 | 88.24 | 82.13 |
| 9 | — | 90.36 | 92.96 | 88.28 |
| 10 | — | 92.69 | 95.47 | 91.68 |
| 11 | — | 94.87 | 97.57 | 94.02 |
| 12 | — | 96.14 | 98.39 | 95.67 |
| 13 | — | 97.37 | 99.23 | 96.93 |
| 14 | — | 98.21 | 99.69 | 97.56 |
| 15 | — | 98.71 | 99.97 | 98.33 |
| 16 | — | 99.47 | 100.37 | 98.83 |

A study was done to determine the effect of curing temperature and time on drug dissolution. The curing temperature was set at 55° C. for 5 and 16 hours. The effect on the dissolution of the drug at a curing temperatures of 70° C. for about 2 hours was also determined. Dissolution tests of the coated tablets under the different curing temperatures and lengths of time were carried under the following dissolution conditions:

Medium: 900 ml water.
Method: USP Type II Apparatus, 50 rpm at 37° C.

The results are presented in Table 3 as a % release into the medium of the total metformin HCl in the tablet:

TABLE 3

| Time (h) | Tablet Cores | MC (55° C.-5 hr) | MC (55° C.-16 hr) | MC (70° C.-2 hr) |
| --- | --- | --- | --- | --- |
| 0 | 0 | 0 | 0 | 0 |
| 1 | 103.92 | 13.08 | 11.86 | 7.04 |
| 2 | — | 37.54 | 32.76 | 16.59 |
| 3 | — | 54.51 | 54.39 | 26.69 |
| 4 | — | 67.48 | 67.85 | 38.02 |
| 5 | — | 78.38 | 78.89 | 50.56 |
| 6 | — | 87.14 | 88.15 | 63.31 |
| 7 | — | 93.31 | 93.43 | 74.98 |
| 8 | — | 96.5 | 96.12 | 84.71 |
| 9 | — | 98.11 | 97.55 | 91.92 |
| 10 | — | 99.11 | 98.36 | 96.47 |
| 11 | — | 99.51 | 98.82 | 99.45 |
| 12 | — | 99.91 | 99.13 | 101.21 |

The influence of the coat on different dissolution media relative to water was determined as follows:

Media: water, 0.1 N HCl (pH1.2)+Citramide, or pH5.8 phosphate buffer+Citramide.
Method: USP Type II Apparatus, 50 rpm at 37° C.

The results are presented in Table 4 as a % release into the medium of the total metformin HCl in the tablet:

TABLE 4

| Time (h) | MC water | MB water | MC pH 5.8 + Citramide | MC pH 1.2 + Citramide | MB pH 5.8 + Citramide | MB pH 1.2 + Citramide |
| --- | --- | --- | --- | --- | --- | --- |
| 0 | 0 | 0 | 0 | 0 | 0 | 0 |
| 1 | 7.04 | 11.26 | 5.62 | 5.74 | 8.61 | 8.98 |
| 2 | 16.59 | 24.4 | 13.28 | 13.39 | 19.69 | 20.58 |
| 3 | 26.69 | 38.12 | 20.99 | 20.83 | 31.23 | 31.96 |

TABLE 4-continued

| Time (h) | MC water | MB water | MC pH 5.8 + Citramide | MC pH 1.2 + Citramide | MB pH 5.8 + Citramide | MB pH 1.2 + Citramide |
|---|---|---|---|---|---|---|
| 4 | 38.02 | 52.75 | 29.47 | 28.94 | 43.42 | 43.46 |
| 5 | 50.56 | 66.73 | 38.99 | 37.84 | 56.09 | 54.97 |
| 6 | 63.31 | 79.25 | 49.47 | 47.76 | 68.35 | 66.08 |
| 7 | 74.98 | 88.78 | 60.68 | 58.06 | 78.89 | 76.22 |
| 8 | 84.71 | 95.41 | 72.25 | 68.75 | 86.79 | 84.81 |
| 9 | 91.92 | 99.42 | 81.02 | 77.34 | 92.06 | 89.75 |
| 10 | 96.47 | 101.76 | 86.63 | 83.99 | 95.01 | 92.56 |
| 11 | 99.45 | 103.05 | 90.01 | 87.32 | 96.72 | 94.64 |
| 12 | 101.21 | 103.86 | 92.45 | 90.03 | 97.77 | 95.52 |
| 13 | 102.36 | 104.25 | 94.27 | 92.21 | 98.49 | 96.58 |
| 14 | 103.38 | | 95.51 | 93.2 | 98.97 | 96.79 |
| 15 | 104.06 | | 96.61 | 94.45 | 99.34 | 97.45 |
| 16 | 104.77 | | 97.46 | 95.47 | 99.6 | 97.74 |

The stability of the tablet coated with formulation MD coated to 16% weight gain stored at 40° C./75% relative humidity (RH) was determined at periodic intervals over a 12 month period by determining the dissolution of the metformin under the following conditions:

Media: 900 ml water

Method: USP Type 11 Apparatus, 50 rpm at 37° C.

The dissolution data is presented in Table 5 as a % release into the medium of the total metformin HCl in the tablet:

TABLE 5

| Time (h) | 0 Month | 1 Month | 2 Month | 3 Month | 6 Month | 12 Month |
|---|---|---|---|---|---|---|
| 1 | 7 | 5.3 | 7.3 | 8.3 | 3.3 | 9.7 |
| 2 | 16.6 | 13.8 | 16.9 | 19.1 | 13.4 | 21.4 |
| 4 | 38 | 35 | 39.7 | 46.8 | 38 | 49.7 |
| 8 | 84.7 | 79 | 87.3 | 98.1 | 89.4 | 92.9 |
| 12 | 101.2 | 90.4 | 99.4 | 106.8 | 102.8 | 99.9 |

A comparative study was conducted to determine the bioavailability following administration of a single dose metformin tablet (Tables 6 and 7) or multiple-dose metformin tablet (Table 8) of the invention

TABLE 6

| Time (Hrs) | Metformin HCl 500 mg ER Tablets, q.d. (Lot # 00F167) | Metformin HCl 500 mg ER Tablets, q.d. (Lot # 07(C)/00 500 XL-HT)) | Glucophage 500 mg, b.i.d. (Lot # C8J247A) |
|---|---|---|---|
| 0 | 0.00 ± 0.00 | 12.68 ± 39.85 | 2.51 ± 9.71 |
| 2 | 7.37 ± 15.46 | 53.96 ± 31.93 | 73.39 ± 59.00 |
| 4 | 343.92 ± 146.45 | 164.46 ± 65.57 | 200.20 ± 114.59 |
| 5 | 476.22 ± 151.89 | 176.46 ± 80.87 | 485.69 ± 188.37 |
| 6 | 390.96 ± 129.93 | 146.23 ± 65.48 | 630.49 ± 161.58 |
| 7 | 325.99 ± 104.84 | 116.62 ± 59.84 | 707.85 ± 215.67 |
| 8 | 284.59 ± 104.39 | 97.20 ± 51.97 | 651.46 ± 183.34 |
| 9 | 242.05 ± 95.88 | 85.26 ± 47.76 | 466.04 ± 128.06 |
| 10 | 204.51 ± 86.24 | 77.24 ± 43.17 | 259.19 ± 78.14 |
| 12 | 127.37 ± 62.84 | 49.53 ± 28.71 | 158.77 ± 42.42 |
| 16 | 60.11 ± 37.32 | 21.02 ± 19.97 | 55.69 ± 16.58 |
| 20 | 40.52 ± 30.87 | 15.63 ± 16.54 | 25.93 ± 19.96 |
| 24 | 19.64 ± 23.26 | 9.49 ± 14.00 | 6.01 ± 12.75 |

TABLE 7

| SUBJECT | Metformin HCl 500 mg ER Tablets, q.d. (Lot # 00F167) | | | Metformin HCl 500 mg ER Tablets, q.d. (Lot #07(C)/00 500 XL-HT)) | | | Glucophage 500 mg, b.i.d. (Lot # C8J247A) | | |
|---|---|---|---|---|---|---|---|---|---|
| | $C_{max}$ | $AUC_{0-t}$ | $T_{max}$ | $C_{max}$ | $AUC_{0-t}$ | $T_{max}$ | $C_{max}$ | $AUC_{0-t}$ | $T_{max}$ |
| 1 | 423.94 | 3203.04 | 5.0 | 296.51 | 1589.86 | 5.0 | 901.58 | 5608.64 | 3.0 |
| 2 | 357.51 | 4267.79 | 10.0 | | | | | | |
| 3 | 318.39 | 1602.89 | 5.0 | 216.55 | 1842.90 | 5.0 | 447.61 | 2971.16 | 5.0 |
| 4 | 489.60 | 2784.57 | 4.0 | 127.03 | 1447.85 | 4.0 | 510.26 | 3504.43 | 4.0 |
| 5 | 592.40 | 3864.41 | 5.0 | 166.35 | 1484.23 | 5.0 | 735.54 | 5394.77 | 4.0 |
| 6 | 414.96 | 2295.36 | 5.0 | 175.21 | 1285.79 | 5.0 | 686.09 | 4258.03 | 4.0 |
| 7 | 419.53 | 3619.34 | 5.0 | 191.15 | 1415.17 | 5.0 | 520.19 | 3435.10 | 3.0 |
| 8 | 227.86 | 1548.93 | 5.0 | 203.87 | 1373.32 | 4.0 | 806.18 | 5076.93 | 3.0 |
| 9 | 664.24 | 4366.66 | 5.0 | 187.89 | 1779.67 | 5.0 | 697.26 | 4994.51 | 2.0 |
| 10 | 583.18 | 3398.15 | 5.0 | 144.69 | 978.64 | 5.0 | 1002.36 | 6098.66 | 4.0 |
| 11 | 566.79 | 5048.15 | 6.0 | 173.95 | 1771.12 | 6.0 | 641.14 | 4709.57 | 5.0 |
| 12 | 573.18 | 3370.02 | 5.0 | 42.10 | 236.63 | 4.0 | 654.03 | 4208.54 | 4.0 |
| 13 | 302.20 | 2559.23 | 5.0 | 192.13 | 2090.60 | 5.0 | 586.54 | 4177.75 | 4.0 |
| 14 | | | | 158.98 | 1152.05 | 4.0 | 1090.92 | 6671.03 | 5.0 |
| 16 | 625.70 | 4278.32 | 5.0 | 152.38 | 930.85 | 0.0 | 808.43 | 4882.53 | 4.0 |
| 19 | 640.76 | 3353.70 | 4.0 | 123.43 | 496.15 | 5.0 | 578.89 | 3108.53 | 2.0 |
| 20 | 768.94 | 4284.70 | 5.0 | 396.18 | 2689.22 | 5.0 | 1125.20 | 6308.03 | 4.0 |
| Mean | 498.1 | 3365.33 | 5.3 | 184.3 | 1410.25 | 4.5 | 737.0 | 4713.01 | 3.8 |
| SD | 151.9 | 1006.86 | 1.3 | 77.4 | 594.66 | 1.3 | 205.5 | 1133.00 | 0.9 |
| CV (%) | 30.5 | 29.92 | 25.6 | 42.0 | 42.17 | 29.3 | 27.9 | 24.04 | 24.8 |
| GeoMean | 474.1 | 3199.36 | 5.1 | 168.4 | 1247.38 | 4.8 | 711.4 | 4581.55 | 3.6 |
| Min | 227.86 | 1548.93 | 4.00 | 42.10 | 236.63 | 0.00 | 447.61 | 2971.16 | 2.00 |
| Max | 768.94 | 5048.15 | 10.00 | 396.18 | 2689.22 | 6.00 | 1125.20 | 6671.03 | 5.00 |

TABLE 8

| SUBJECT | Metformin HCl 500 mg ER Tablets, q.d. (Lot # 00F167) | | | Metformin HCl 500 mg ER Tablets, q.d. (Lot #07(C)/ 00 500 XL-HT)) | | | Glucophage 500 mg, b.i.d. (Lot # C8J247A) | | |
|---|---|---|---|---|---|---|---|---|---|
| | $C_{max}$ | $AUC_{0-\tau}$ | $T_{max}$ | $C_{max}$ | $AUC_{0-\tau}$ | $T_{max}$ | $C_{max}$ | $AUC_{0-\tau}$ | $T_{max}$ |
| 1 | 945.40 | 6232.57 | 5.0 | 872.61 | 5177.02 | 5.0 | 886.47 | 12899.68 | 3.0 |
| 3 | 722.90 | 8312.65 | 5.0 | 475.83 | 4403.99 | 5.0 | 628.12 | 10229.16 | 15.0 |
| 4 | 540.79 | 4332.49 | 4.0 | 155.28 | 1538.15 | 4.0 | 580.82 | 7692.77 | 3.0 |
| 5 | 1562.92 | 10130.87 | 5.0 | 401.35 | 3980.27 | 5.0 | 968.26 | 12011.86 | 3.0 |
| 6 | 770.21 | 5346.86 | 6.0 | 425.47 | 3514.28 | 4.0 | 821.17 | 10603.35 | 3.0 |
| 7 | 560.34 | 4490.96 | 5.0 | 409.97 | 3884.59 | 5.0 | 721.95 | 10518.02 | 4.0 |
| 8 | 1105.38 | 8133.56 | 5.0 | 442.39 | 4111.28 | 5.0 | 757.45 | 11971.60 | 4.0 |
| 9 | 727.04 | 4863.71 | 5.0 | 541.01 | 5228.69 | 5.0 | 977.96 | 12244.88 | 4.0 |
| 10 | 1150.00 | 7974.91 | 5.0 | 694.61 | 4673.33 | 5.0 | 1123.79 | 14656.81 | 4.0 |
| 11 | 983.35 | 6791.08 | 5.0 | 594.71 | 5228.49 | 6.0 | 817.43 | 10463.89 | 5.0 |
| 12 | 961.04 | 6548.23 | 5.0 | 454.24 | 4037.80 | 5.0 | 856.27 | 11769.61 | 4.0 |
| 13 | 963.88 | 8612.93 | 6.0 | 430.68 | 4788.57 | 5.0 | 734.24 | 12074.02 | 4.0 |
| 14 | | | | 615.73 | 5939.67 | 5.0 | | | |
| 16 | 990.87 | 5890.99 | 5.0 | 359.87 | 3273.11 | 5.0 | 567.54 | 7890.22 | 3.0 |
| 19 | 835.28 | 4797.61 | 4.0 | 368.31 | 2801.78 | 4.0 | 893.94 | 11735.13 | 4.0 |
| 20 | 3835.55 | 11037.19 | 6.0 | 774.96 | 6522.10 | 5.0 | 970.78 | 15109.04 | 6.0 |
| Mean | 1110.3 | 6899.77 | 5.1 | 501.1 | 4318.94 | 4.9 | 820.4 | 11458.00 | 4.6 |
| SD | 795.1 | 2072.53 | 0.6 | 176.3 | 1222.75 | 0.5 | 158.5 | 2042.45 | 3.0 |
| CV (%) | 71.6 | 30.04 | 11.7 | 35.2 | 28.31 | 10.3 | 19.3 | 17.83 | 65.1 |
| GeoMean | 973.3 | 6620.63 | 5.0 | 469.2 | 4119.36 | 4.8 | 805.7 | 11278.47 | 4.1 |
| Min | 540.79 | 4332.49 | 4.00 | 155.28 | 1538.15 | 4.00 | 567.54 | 7692.77 | 3.00 |
| Max | 3835.55 | 11037.19 | 6.00 | 872.61 | 6522.10 | 6.00 | 1123.79 | 15109.04 | 15.00 |

EXAMPLE 2

Bupropion HCl Tablets 2.1 Tablet Core Preparation

The following formulation was prepared for Bupropion HCl 300 mg and 150 mg strength tablets:

| Ingredients | % w/w |
|---|---|
| Bupropion HCl | 93.75 |
| Polyvinyl alcohol (PVA)* | 3.31 |
| Atomized Glyceryl Behenate** | 2.94 |
| Total | 100.00 |

**The PVA is prepared as a 4.6% solution (w/w) in purified water. The purified water is not considered as part of the theoretical batch size since it is evaporated during drying of the core in the fluid bed granulator.
***Compritol 888 ATO The tablet cores were prepared as described above for oxycodone HCl. The granules were compressed into either 320 mg tablets (for 300 mg strength tablets) or 160 mg tablets (for 150 mg strength tablets). The dissolution profile of the compressed tablets was determined under the following conditions:

Medium: 900 ml water

Method: USP Type II Apparatus, 50 rpm at 37° C.

The release of bupropion HCl from the tablet cores was found to be about 100% in about 30 minutes.

2.2 Core Coating

The following four coating formulations were prepared for the bupropion HCl 300 mg strength tablet cores:

| Ingredients | BA (% w/w) | BB (% w/w) | BC (% w/w) | BD (% w/w) | BE (% w/w) |
|---|---|---|---|---|---|
| Eudrgit NE 30D(Liquid) | 26.82 | 26.82 | 26.82 | 26.82 | 26.82 |
| Talc 400 | 4.83 | 4.02 | 3.62 | 4.43 | 4.02 |
| Titanium Dioxide | 0.81 | 0.81 | 0.81 | 0.81 | 0.81 |
| HPMC | 2.01 | 2.82 | 3.22 | 2.41 | 2.82 |
| PEG 8000 | 2.01 | 2.01 | 2.01 | 2.01 | 2.01 |
| Simethicone | 0.2 | 0.2 | 0.2 | 0.2 | 0.2 |
| Tween 80 | 0.1 | 0.1 | 0.1 | 0.1 | 0.1 |
| Purified water | 63.22 | 63.22 | 63.22 | 63.22 | 63.22 |
| Total | 100.00 | 100.00 | 100.00 | 100.00 | 100.00 |

The following two coating formulations were prepared for the bupropion HCl 150 mg strength tablet cores:

| Ingredients | BF (w/w %) | BG (% w/w) |
|---|---|---|
| Eudrgit NE 30D(Liquid) | 26.82 | 26.82 |
| Talc 400 | 4.02 | 3.62 |
| Titanium Dioxide | 0.81 | 0.81 |
| HPMC 606 | 2.82 | 3.22 |
| PEG 8000 | 2.01 | 2.01 |
| Somethicone | 0.2 | 0.2 |
| Tween 80 | 0.1 | 0.1 |
| Purified water | 63.22 | 63.22 |
| Total | 100.00 | 100.00 |

The bupropion HCl 300 mg core tablets were coated with either one of the coat formulations BA-BE to 15% weight gain as described for the metformin HCl core tablets. Coated tablet cores were cured at 62±2° C. Dissolution tests of the coated tablet cores was carried out under the following dissolution conditions:

Medium: 900 ml 0.1 N HCl or water

Method: USP Type I Apparatus, 75 rpm at 37° C.

The results are presented in Table 9 and 10 as a % release into 0.1 N HCl and water respectively of the total bupropion HCl in the 300 mg tablet:

TABLE 9

| Time (h) | BB | BC | BD | BE |
|---|---|---|---|---|
| 0 | 0 | 0 | 0 | 0 |
| 1 | 2.6 | 4.18 | 1.73 | 2.2 |
| 2 | 5.9 | 9.03 | 4.23 | 4.58 |
| 3 | 9 | 14.3 | 6.44 | 6.62 |
| 4 | 12 | 19.89 | 8.43 | 10.25 |
| 5 | 15.5 | 27.23 | 10.44 | 12.93 |
| 6 | 19.3 | 33.14 | 12.6 | 16.65 |
| 7 | 23.7 | 40.45 | 14.9 | 20.43 |
| 8 | 28.5 | 46.81 | 17.32 | 24.39 |
| 9 | 33.7 | 52.46 | 20.04 | 29.24 |
| 10 | 39.1 | 59.59 | 23 | 34.72 |
| 11 | 44.5 | 64.57 | 26.3 | 38.98 |
| 12 | 49.9 | 69.7 | 29.84 | 44.62 |
| 13 | 55 | 74.6 | 33.66 | 47.26 |
| 14 | 59.9 | 78.17 | 37.69 | 51.94 |
| 15 | 64.5 | 81.99 | 41.85 | 56.03 |
| 16 | 69 | 85.05 | 46.37 | 60.72 |
| 17 |  | 88.58 | 50.72 | 63.61 |
| 18 |  | 91.14 | 54.7 | 67.4 |
| 19 |  | 92.25 | 58.4 | 70.4 |
| 20 |  | 93.62 | 62.1 | 73.93 |
| 21 |  | 94.86 | 65.6 | 76.55 |
| 22 |  | 95.72 | 68.9 | 77.86 |
| 23 |  | 96.25 | 72.1 | 79.97 |
| 24 |  | 96.69 | 75.1 | 82.32 |

TABLE 10

| Time (h) | BA | BB | BC | BD | BE |
|---|---|---|---|---|---|
| 0 | 0 | 0 | 0 | 0 | 0 |
| 1 | 1 | 1.97 | 4.62 | 1.6 | 2.4 |
| 2 | 2.5 | 4.65 | 8.73 | 3.6 | 5.1 |
| 3 | 3.8 | 7.3 | 12.7 | 5.3 | 7.3 |
| 4 | 4.8 | 9.93 | 17.09 | 6.8 | 9.3 |
| 5 | 5.8 | 12.73 | 21.96 | 8.2 | 11.4 |
| 6 | 6.7 | 16 | 27.37 | 9.6 | 13.5 |
| 7 | 7.6 | 19.3 | 33.18 | 11 | 15.8 |
| 8 | 8.5 | 22.5 | 39.22 | 12.5 | 18.3 |
| 9 | 9.4 | 26 | 45.16 | 14 | 21 |
| 10 | 10.3 | 29.1 | 50.78 | 15.7 | 23.9 |
| 11 | 11.2 | 33.2 | 56.13 | 17.5 | 27.15 |
| 12 | 12.3 | 36.7 | 61.09 | 19.5 | 30.52 |
| 13 | 13.4 | 40.7 | 65.72 | 21.7 | 34.11 |
| 14 | 14.6 | 44.5 | 69.95 | 24.2 | 37.89 |
| 15 | 15.8 | 47.8 | 73.76 | 26.8 | 41.58 |
| 16 | 17.2 | 51.5 | 77.15 | 29.8 | 45.27 |
| 17 |  | 54.9 | 80.1 | 33.3 | 48.91 |
| 18 |  | 58.6 | 82.65 | 37.1 | 52.59 |
| 19 |  | 61.7 | 84.75 | 40.7 | 56.06 |
| 20 |  | 64.7 | 86.51 | 45.6 | 59.35 |
| 21 |  | 68.2 | 87.97 | 50.1 | 62.5 |
| 22 |  | 71.4 | 89.15 | 53.8 | 65.67 |
| 23 |  | 74.3 | 90.12 | 57.3 | 68.49 |
| 24 |  | 77 | 90.96 | 60.4 | 71.1 |

The 150 mg tablet cores were coated with formulations BF and BG to to 15% and 25% weight gain respectively and dissolution tests were performed on these tablets under the following conditions:

Media: 900 ml 0.1 N HCl

Method: USP Type I Apparatus, 75 rpm at 37° C.

The dissolution data is presented in Table 11 as a % release into the medium of the total bupropion HCl:

TABLE 11

| Time (h) | BG (25% weight gain) | BF (15% weight gain) |
|---|---|---|
| 0 | 0 | 0 |
| 1 | 1.61 | 2.89 |
| 2 | 5.75 | 6.9 |
| 3 | 9.89 | 10.83 |
| 4 | 14.3 | 15.3 |
| 5 | 19.3 | 20.38 |
| 6 | 24.58 | 25.98 |
| 7 | 29.97 | 31.91 |
| 8 | 35.18 | 37.86 |
| 9 | 40.18 | 43.79 |
| 10 | 44.87 | 49.29 |
| 11 | 49.33 | 54.64 |
| 12 | 53.55 | 59.58 |
| 13 | 57.49 | 64.28 |
| 14 | 61.33 | 68.63 |
| 15 | 64.87 | 72.65 |
| 16 | 68.24 | 76.34 |
| 17 | 71.41 | 79.71 |
| 18 | 74.32 | 82.7 |
| 19 | 77.05 | 85.31 |
| 20 | 79.55 | 87.52 |
| 21 | 81.84 | 89.38 |
| 22 | 83.92 | 90.97 |
| 23 | 85.64 | 92.34 |
| 24 | 87.31 | 93.47 |

The stability of the tablet coated with formulation BG supplemented with 0.65 titanium dioxide and 0.12% synthetic iron oxide pigment. The tablet was coated to 20% weight gain stored at 40° C./75% relative humidity (RH) was determined at periodic intervals over a 3 month period by determining the dissolution of the bupropion under the following conditions:

Method: 900 ml 0.1 N HCl

Method: USP Type I Apparatus, 75 rpm at 37° C.

The dissolution data is presented in Table 12 as a % release into the medium of the total bupropion HCl in the tablet:

TABLE 12

| Time (h) | 0 Month | 1 Month | 3 Month |
|---|---|---|---|
| 2 | 6.0 | 6.2 | 6.4 |
| 4 | 14.4 | 15.3 | 15.7 |
| 8 | 36.6 | 41.0 | 42.1 |
| 16 | 72.8 | 82.6 | 84.2 |
| 24 | 92.3 | 99.4 | 93.6 |

A comparative study was conducted to determine the bioavailability following administration of a single dose bupropion tablet (Tables 13 and 14) the invention.

TABLE 13

| Time (Hrs) | Bupropion HCl 150 mg ER Tablets. (Lot # Bup-Bio (AQ) 02C-02/150-NE) | Bupropion HCl 150 mg ER Tablets. (Lot # Bup-Bio (AQ) 03A-02/150-S) | Bupropion HCl XL Tablets, 150 mg. (Lot # 02A063) |
|---|---|---|---|
| 0 | 0.00 ± 0.00 | 0.00 ± 0.00 | 0.00 ± 0.00 |
| 0.5 | 0.00 ± 0.00 | 0.00 ± 0.00 | 0.00 ± 0.00 |
| 1 | 0.14 ± 0.51 | 0.00 ± 0.00 | 0.00 ± 0.00 |
| 1.5 | 1.37 ± 1.55 | 0.00 ± 0.00 | 0.00 ± 0.00 |
| 2 | 4.27 ± 2.25 | 0.00 ± 0.00 | 0.81 ± 1.64 |
| 2.5 | 7.14 ± 2.76 | 0.43 ± 0.60 | 3.25 ± 3.40 |

TABLE 13-continued

| Time (Hrs) | Bupropion HCl 150 mg ER Tablets. (Lot # Bup-Bio (AQ) 02C-02/150-NE) | Bupropion HCl 150 mg ER Tablets. (Lot # Bup-Bio (AQ) 03A-02/150-S) | Bupropion HCl XL Tablets, 150 mg. (Lot # 02A063) |
|---|---|---|---|
| 3 | 9.55 ± 3.57 | 1.15 ± 0.96 | 11.56 ± 10.81 |
| 3.5 | 11.49 ± 4.68 | 2.35 ± 1.72 | 22.75 ± 16.54 |
| 4 | 12.12 ± 4.91 | 3.26 ± 2.25 | 30.24 ± 18.87 |
| 4.5 | 13.35 ± 5.35 | 5.37 ± 4.20 | 39.88 ± 23.52 |
| 5 | 17.35 ± 6.80 | 7.27 ± 3.59 | 53.42 ± 20.15 |
| 5.5 | 17.40 ± 6.69 | 8.53 ± 3.34 | 60.76 ± 19.45 |
| 6 | 16.07 ± 5.48 | 9.40 ± 3.82 | 62.08 ± 18.83 |
| 8 | 13.00 ± 5.34 | 8.98 ± 4.17 | 46.47 ± 16.36 |
| 10 | 22.40 ± 10.48 | 16.39 ± 20.64 | 44.23 ± 15.86 |
| 12 | 34.46 ± 13.26 | 18.57 ± 13.43 | 35.14 ± 15.55 |
| 16 | 28.01 ± 9.36 | 27.36 ± 15.05 | 20.40 ± 6.96 |
| 24 | 17.87 ± 8.27 | 19.81 ± 8.32 | 10.11 ± 3.58 |
| 36 | 6.76 ± 3.93 | 8.51 ± 7.13 | 4.94 ± 1.58 |
| 48 | 3.51 ± 1.36 | 4.01 ± 2.26 | 3.41 ± 1.66 |
| 72 | 1.35 ± 0.88 | 1.65 ± 0.83 | 1.21 ± 0.90 |
| 96 | 0.19 ± 0.46 | 0.35 ± 0.55 | 0.21 ± 0.51 |
| 120 | 0.00 ± 0.00 | 0.00 ± 0.00 | 0.00 ± 0.00 |

TABLE 14

| | Bupropion HCl 150 mg ER Tablets. (Lot # Bup-Bio (AQ) 02C-02/150-NE) | | | Bupropion HCl 150 mg ER Tablets. (Lot # Bup-Bio (AQ) 03A-02/150-S) | | | Bupropion HCl XL Tablets, 150 mg. (Lot # 02A063) | | |
|---|---|---|---|---|---|---|---|---|---|
| SUBJECT | AUC | CMAX | TMAX | AUC | CMAX | TMAX | AUC | CMAX | TMAX |
| 1 | 783.88 | 27.72 | 24.0 | 637.03 | 36.23 | 12.0 | 654.49 | 74.73 | 5.5 |
| 2 | 366.41 | 28.05 | 12.0 | 550.51 | 30.78 | 16.0 | 534.11 | 53.70 | 6.0 |
| 3 | 1179.19 | 52.75 | 16.0 | 1223.27 | 86.66 | 10.0 | 1223.86 | 91.77 | 6.0 |
| 4 | 789.01 | 44.01 | 12.0 | 167.84 | 17.49 | 4.5 | 954.87 | 106.52 | 5.5 |
| 5 | 730.90 | 44.92 | 10.0 | 518.11 | 29.30 | 16.0 | 881.67 | 62.52 | 6.0 |
| 7 | 577.62 | 27.97 | 16.0 | 577.76 | 24.60 | 24.0 | 677.27 | 54.21 | 10.0 |
| 8 | 1095.68 | 32.75 | 24.0 | 1094.55 | 32.36 | 24.0 | 1098.80 | 75.11 | 10.0 |
| 9 | 494.33 | 23.05 | 12.0 | 495.00 | 17.49 | 16.0 | 440.79 | 43.58 | 5.5 |
| 10 | 1000.63 | 35.30 | 16.0 | 911.09 | 35.40 | 24.0 | 1093.05 | 70.28 | 5.5 |
| 12 | 837.22 | 32.33 | 12.0 | 877.09 | 23.13 | 36.0 | 747.36 | 50.07 | 5.0 |
| 13 | 855.14 | 46.38 | 12.0 | 911.36 | 58.44 | 16.0 | 836.02 | 69.49 | 6.0 |
| 14 | 806.11 | 55.63 | 12.0 | 572.52 | 21.93 | 16.0 | 1050.24 | 85.35 | 8.0 |
| 15 | 612.93 | 27.04 | 16.0 | 717.12 | 36.47 | 16.0 | 613.25 | 72.73 | 5.5 |
| 16 | 654.03 | 57.51 | 12.0 | 699.39 | 23.97 | 16.0 | 1082.74 | 71.07 | 6.0 |
| Mean | 770.22 | 38.24 | 14.71 | 710.90 | 33.87 | 17.61 | 849.18 | 70.08 | 6.46 |
| Std. Dev | 224.61 | 11.70 | 4.41 | 272.38 | 18.43 | 7.55 | 243.23 | 17.02 | 1.65 |
| CV (%) | 29.16 | 30.58 | 29.97 | 38.32 | 54.41 | 42.85 | 28.64 | 24.29 | 25.47 |
| GeoMean | 737.74 | 36.63 | 14.20 | 650.74 | 30.60 | 16.00 | 814.20 | 68.19 | 6.30 |
| Min | 366.41 | 23.05 | 10.00 | 167.84 | 17.49 | 4.50 | 440.79 | 43.58 | 5.00 |
| Max | 1179.19 | 57.51 | 24.00 | 1223.27 | 86.66 | 36.00 | 1223.86 | 106.52 | 10.00 |

EXAMPLE 3

Tramadol HCl Tablets

3.1 Tablet Core Preparation

The following formulation was prepared for tramadol HCl 40 mg or 80 mg strength tablets:

| Ingredients | % w/w | % w/w |
|---|---|---|
| Tramadol HCl | 40.0 | 80.0 |
| Silicon Dioxide* | 0.4 | 0.4 |
| Polyvinyl alcohol (PVA)** | 1.1 | 0.9 |
| Lactose Anhydrous DT | 56.5 | 16.69 |
| Atomized Glyceryl Behenate*** | 2.00 | 2.00 |
| Total | 100.00 | 100.00 |

*Aerosil 200.
**The PVA is prepared as a 3.8% solution (w/w) in purified water. The purified water is not considered as part of the theoretical batch size since it is evaporated during drying of the core in the fluid bed granulator.
***Compritol 888 ATO All of the ingredients were transferred into a V-blender and processed as described above for metformin HCl. The granules were subsequently compressed into tablets.

The dissolution profile of the compressed tablet cores was determined under following conditions:

Medium: 900 ml water
Method: USP Type II Apparatus, 75 rpm at 37° C.

The tablet cores are immediate release. The release of tramadol HCl from the tablet cores was found to be 100% in about 30 min.

3.2 Core Coating

The following four coat formulations were prepared:

| Ingredients | TA (% w/w) | TB (% w/w) | TC (% w/w) | TD (% w/w) |
|---|---|---|---|---|
| Eudrgit NE 30D(Liquid) | 38.5 | 33.3 | 27.74 | 28.82 |
| Talc 400 | 4.7 | 4.21 | 4.14 | 4.32 |
| Titanium Dioxide | 1.6 | 1.35 | 1.2 | 1.24 |
| HPMC 606 | 1.4 | 1.35 | 1.02 | 1.05 |
| PEG 8000 | 0 | 1.18 | 0 | 0.43 |
| Simethicone | 0.32 | 0.25 | 0.2 | 0.21 |

-continued

| Ingredients | TA (% w/w) | TB (% w/w) | TC (% w/w) | TD (% w/w) |
|---|---|---|---|---|
| Tween 80 | 0.24 | 0.2 | 0.12 | 0.12 |
| Purified water | 53.24 | 58.16 | 65.58 | 63.81 |
| Total | 100 | 100 | 100 | 100 |

The coating procedure was carried out as described above for metformin HCl tablet cores. Coated tablet cores were cured at 62±° C. for about 2 hours.

The tramadol tablet cores were coated with either one of the coating formulations TA, TB, TC, and TD. The coating was applied to a weight gain of approximately 8% to about 18%. Curing temperatures ranged from about 60° C. to about 65° C. and curing times were for either 3 or 4 hours. Dissolution tests were carried out as follows:
  Medium: 900 ml 0.1 N HCl (pH 1.2)
  Method: USP Type I Apparatus, 75 rpm at 37° C.

The dissolution data is presented in Table 15 as a % release into the medium of the total tramadol HCl:

TABLE 15

| Time (h) | TD (8% weight gain, cured at 65° C. for 3 hrs) | TC (8% weight gain, cured at 60° C. for 3 hrs) | TB (13% weight gain, cured at 60° C. for 4 hrs) | TA (18% weight gain, cured at 60° C. for 3 hrs) |
|---|---|---|---|---|
| 0 | 0 | 0 | 0 | 0 |
| 1 | 1.15 | 1.64 | 0.29 | 1.31 |
| 2 | 3.05 | 5.16 | 0.44 | 1.94 |
| 3 | 5.48 | 10.83 | 0.89 | 2.5 |
| 4 | 8.32 | 21.09 | 1.73 | 3.23 |
| 5 | 11.26 | 37.21 | 2.89 | 3.92 |
| 6 | 15.07 | 51.97 | 4.1 | 4.93 |
| 7 | 20 | 65.54 | 5.32 | 5.94 |
| 8 | 25.01 | 76.21 | 6.55 | 6.97 |
| 9 | 30.96 | 83.67 | 7.92 | 8.24 |
| 10 | 36.99 | 90.23 | 9.22 | 9.65 |
| 11 | 43.48 | 94.47 | 10.58 | 12.1 |
| 12 | 49.4 | 97.8 | 12.07 | 17.08 |
| 13 | 55.33 | 100.02 | 13.55 | 21.78 |
| 14 | 60.97 | 101.6 | 15.25 | 31.93 |
| 15 | 66.43 | 102.66 | 17.02 | 38.89 |
| 16 | 71.33 | 103.39 | 19.12 | 44.12 |
| 17 | 76.25 | 103.92 | 21.3 | 48.31 |
| 18 | 80.54 | — | 23.76 | 52.18 |
| 19 | 84.05 | — | 26.36 | 55.78 |
| 20 | 87.18 | — | 28.93 | 58.96 |
| 21 | 89.85 | — | 31.48 | 61.62 |
| 22 | 91.87 | — | — | 64.63 |
| 23 | 93.65 | — | — | 66.97 |
| 24 | 95.2 | — | — | 69.54 |

Tablets coated with formulation TC were cured at either 60° C. for 3 hrs or for 22 hours at 70° C. for 3 hrs. Dissolution tests were conducted as follows:
  Media: 900 ml 0.1 N HCl
  Method: USP Type I Apparatus, 75 rpm at 37° C.

The dissolution data is presented in Table 16 as a % release into the medium of the total tramadol HCl:

TABLE 16

| Time (h) | TC cured at 60° C. for 22 hrs | TC cured at 70° C. for 3 hrs. | TC cured at 60° C. for 3 hrs |
|---|---|---|---|
| 0 | 0 | 0 | 0 |
| 1 | 1.4032 | 1.3888 | 1.64 |
| 2 | 3.9566 | 3.8022 | 5.16 |
| 3 | 7.9378 | 7.3746 | 10.83 |
| 4 | 13.631 | 12.784 | 21.09 |
| 5 | 21.956 | 20.607 | 37.21 |
| 6 | 32.55 | 31.338 | 51.97 |
| 7 | 44.124 | 42.846 | 65.54 |
| 8 | 54.9 | 53.873 | 76.21 |
| 9 | 64.3 | 63.568 | 83.67 |
| 10 | 73 | 71.219 | 90.23 |
| 11 | 79.5 | 77.418 | 94.47 |
| 12 | 84 | 82.787 | 97.8 |
| 13 | 88.5 | 86.683 | 100.02 |
| 14 | 91.5 | 89.748 | 101.6 |
| 15 | 94 | 92.209 | 102.66 |
| 16 | 96 | 94.006 | 103.39 |
| 17 | 97.7 | 95.484 | 103.92 |
| 18 | 98.9 | 96.959 | |
| 19 | 100 | 97.853 | |
| 20 | 100.6 | 98.695 | |
| 21 | 101.4 | 99.294 | |
| 22 | 101.9 | | |
| 23 | 102.4 | | |
| 24 | 102.6 | | |

The 80 mg tramadol tablet core was coated to about 8% weight gain with formulation TD and cured at about 65° C. for about 3 hours. Dissolution tests on the tablets was conducted under the following conditions:
  Media: 900 ml, 0.1 N HCl, pH 5.8 phosphate buffer or pH 6.8 phosphate buffer.
  Method: USP Type I Apparatus, 75 rpm at 37° C.

The dissolution data is presented in Table 17 as a % release into the medium of the total tramadol HCl:

TABLE 17

| Time (h) | TD-pH1.2 | TD-pH5.8 | TD-pH6.8 |
|---|---|---|---|
| 0 | 0 | 0 | 0 |
| 1 | 0.58 | 0.5 | 0.44 |
| 2 | 1.49 | 1.96 | 1.61 |
| 3 | 2.66 | 3.81 | 2.84 |
| 4 | 4.12 | 6.2 | 4.58 |
| 5 | 6.18 | 7.79 | 6.99 |
| 6 | 9.34 | 12.6 | 11.16 |
| 7 | 14.43 | 18.73 | 19.19 |
| 8 | 22.98 | 28.78 | 32.31 |
| 9 | 34.85 | 42.14 | 48.55 |
| 10 | 49.13 | 55.48 | 62.39 |
| 11 | 62.65 | 65.45 | 71.68 |
| 12 | 73.37 | 72.39 | 78.03 |
| 13 | 81.08 | 77.11 | 82.39 |
| 14 | 85.36 | 80.71 | 85.52 |
| 15 | 88.37 | 83.36 | 87.77 |
| 16 | 90.66 | 85.54 | 89.72 |
| 17 | 92.34 | 87.33 | 91.14 |
| 18 | 93.79 | 88.83 | 92.42 |
| 19 | 94.92 | 89.9 | 93.44 |
| 20 | 95.74 | 91.04 | 94.3 |
| 21 | 96.36 | 91.72 | 95.08 |
| 22 | 96.97 | 92.63 | 95.65 |
| 23 | 97.51 | 93.11 | 96.25 |
| 24 | 97.94 | 93.68 | 96.78 |

The invention claimed is:
1. A pharmaceutical oral dosage form comprising an oral dosage form coated with a stable controlled release monolithic coating, wherein the stable controlled release monolithic coating is applied onto the oral dosage form by a process comprising
   coating the oral dosage form with a coating composition to form a coated oral dosage form, and curing the coated oral dosage form at a temperature of at least 55° C. to form the stable controlled release monolithic coating, wherein the coating composition consists essentially of a neutral ester copolymer in an amount of from about 1% to about 35% by weight of the coating composition based on ethyl acrylate and methyl acrylate selected from the group consisting of a 30% aqueous dispersion of a neutral ester copolymer based on ethyl acrylate and methyl methacrylate, a 40% aqueous dispersion of a neutral ester copolymer based on ethyl acrylate and methyl methacrylate, and combinations thereof;

a polyethylene glycol selected from the group consisting of polyethylene glycol 6000, polyethylene glycol 8000, polyethylene glycol 10000, polyethylene glycol 20000, and combinations thereof in an amount of from about 0.1% to about 3% by weight of the coating composition; and one or more of a hydrophilic agent, and a pharmaceutically acceptable excipient.

2. The pharmaceutical dosage form of claim 1, wherein said pharmaceutical dosage form is selected from the group consisting of a tablet and a capsule.

3. The pharmaceutical oral dosage form of claim 1, wherein the oral dosage form comprises metformin, a pharmaceutically acceptable salt thereof, or a combination thereof.

4. A method of manufacturing a pharmaceutical oral dosage form coated with a stable controlled release monolithic coating, the method comprising coating the oral dosage form with a coating composition to form a coated oral dosage form, and curing the coated oral dosage form at a temperature of at least 55° C. to form the stable controlled release monolithic coating, wherein the coating composition consists essentially of a neutral ester copolymer based on ethyl acrylate and methyl acrylate selected from the group consisting of a 30% aqueous dispersion of a neutral ester copolymer based on ethyl acrylate and methyl methacrylate, a 40% aqueous dispersion of a neutral ester copolymer based on ethyl acrylate and methyl methacrylate, and combinations thereof in an amount of from about 1% to about 35% by weight of the coating composition;

a polyethylene glycol selected from the group consisting of polyethylene glycol 6000, polyethylene glycol 8000, polyethylene glycol 10000, polyethylene glycol 20000, and combinations thereof in an amount of from about 0.1% to about 3% by weight of the coating composition; and one or more of a hydrophilic agent, and a pharmaceutically acceptable excipient.

5. The method of claim 4, wherein said pharmaceutical dosage form is selected from the group consisting of a tablet and a capsule.

6. The method of claim 4, wherein the oral dosage form comprises metformin, a pharmaceutically acceptable salt thereof, or a combination thereof.

* * * * *